(12) United States Patent
O'Rear

(10) Patent No.: US 8,685,686 B2
(45) Date of Patent: Apr. 1, 2014

(54) BIOFUELS PROCESSES INTEGRATING PHOTOBIOREACTORS WITH ANAEROBIC DIGESTION

(75) Inventor: Dennis J. O'Rear, Penngrove, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 780 days.

(21) Appl. No.: 12/338,360

(22) Filed: Dec. 18, 2008

(65) Prior Publication Data

US 2010/0159554 A1 Jun. 24, 2010

(51) Int. Cl.
*C12P 5/02* (2006.01)

(52) U.S. Cl.
USPC .......................... 435/167; 435/157; 435/168

(58) Field of Classification Search
None
See application file for complete search history.

(56) References Cited

U.S. PATENT DOCUMENTS

| | | | | |
|---|---|---|---|---|
| 4,826,769 A * | 5/1989 | Menger | ................ | 435/167 |
| 4,845,034 A | 7/1989 | Menger et al. | | |
| 8,076,122 B2 | 12/2011 | O'Rear | | |
| 2008/0050800 A1 | 2/2008 | McKeeman et al. | | |

FOREIGN PATENT DOCUMENTS

| WO | 2009063296 | 5/2009 |
|---|---|---|
| WO | WO 2009/063296 | 5/2009 |
| WO | 2009142765 | 11/2009 |
| WO | WO 2009/142765 | 11/2009 |

OTHER PUBLICATIONS

Chisti, Y., Biotechnology Advances, 2007, vol. 25, p. 294-306.*
Shelef, G., 1979, "The combination of algal and anaerobic waste treatment in bioregenerative farm system", 8 page PDF.*
Shelef, G. (1979, "The combination of algal and anaerobic waste treatment in bioregenerative farm system", 9 pages in PDF, citation page 8 of PDF.*
International Search Report and Written Opinion, International Application No. PCT/US2009/068271, dated Aug. 2, 2010.
George W. Huber et al., "Synthesis of Transportation Fuels from Biomass: Chemistry, Catalysts and Engineering", Chem. Rev. 105, pp. 4044-4098 (2006).
Yanqun Li et al., "Biofuels from Microalgae", Biotechnol. Prog. 24, pp. 815-820 (Aug. 8, 2008).
Supplementary European Search Report, International Application No. PCT/US2009/068271, dated Mar. 20, 2013.
Kapdan, I.K. et al.: "Bio-hydrogen production from waste materials," Enzyme and Microbial Technology, Stoneham, MA, US; vol. 38, No. 5, Mar. 2, 2006, pp. 569-582.
Cantrell, K.B. et al.: "Livestock waste-to-bioenergy generation opportunities," Bioresource Technology, Elsevier BV, GB, vol. 99, No. 17, Nov. 1, 2008, pp. 7941-7953.
Kapdan, I.K., et al: "Bio-hydrogen production from waste materials," Enzyme and Microbial Technology, Stoneham, MA, US, vol. 38, No. 5, Mar. 2, 2006, pp. 569-582, ISSN 0141-0229.
Cantrell, K.B., et al: "Livestock waste-to-bionergy generation opportunities," Bioresource Technology, Elsevier BV, GB, vol. 99, No. 17, Nov. 1, 2008, pp. 7941-7953, ISSN 0960-8524.
European Supplemental Search Report of corresponding counterpart European application No. 09837897 dated Mar. 12, 2013.

* cited by examiner

*Primary Examiner* — Kade Ariani

(57) ABSTRACT

In the present invention, integrated processes for producing a biofuel are disclosed. Specifically, processes integrating photobioreactors with anaerobic digestion are disclosed. Anaerobic digestion can convert biomass into a biofuel. However, anaerobic digestion also produces carbon dioxide ($CO_2$). Because it is a greenhouse gas, the production of carbon dioxide is not desirable. Algae can be grown in a photobioreactor as long as light, carbon dioxide, and water are provided. In the present invention, the anaerobic digestion process is integrated with the photobioreactor process thereby providing a useful solution for the carbon dioxide that is generated and providing a source of carbon dioxide for the photobioreactor.

16 Claims, 1 Drawing Sheet

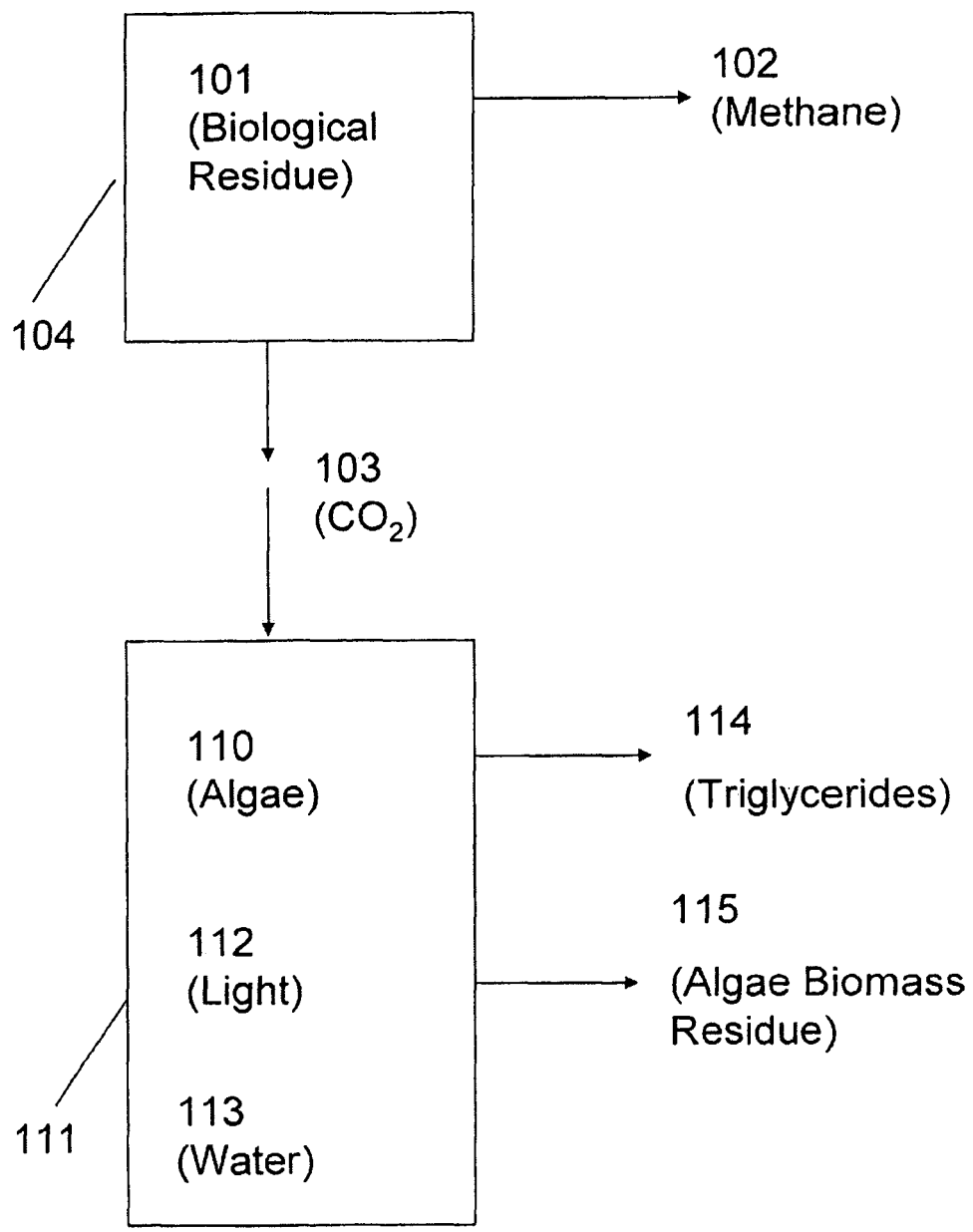

BIOFUELS PROCESSES INTEGRATING PHOTOBIOREACTORS WITH ANAEROBIC DIGESTION

FIELD OF THE INVENTION

The present invention relates generally to processes for generating biofuels and specifically to processes for integrating photobioreactors with anaerobic digestion for the purpose of generating biofuels.

BACKGROUND OF THE INVENTION

As a renewable energy source, the generation of biofuels is of great interest. Biofuels can be categorized according to their feedstock. The feedstock for first generation biofuels includes sugar, starch, vegetable oils, and animal fats. The feedstock for second generation biofuels includes non-food crops.

For second generation biofuels, non-food crops are converted into biofuels. Both the source of the biomass and the conversion processes for second generation biofuels are numerous. One example of a conversion process is anaerobic digestion. One by-product of the anaerobic digestion processes is carbon dioxide ($CO_2$), a greenhouse gas. Concerns over emissions of carbon dioxide are well known.

One example of a source of biomass for second generation biofuels is algae. Algae contain oil that can be converted into a biofuel. Algae require the following three components to grow: light, carbon dioxide, and water. In order to generate algae to be used as a biofuels feedstock, the algae could be grown in multiple different types of environments as long as the above components are present. Algae can be grown in an open environment such as a tank or pond. Alternatively, algae can be grown in a closed environment such as a photobioreactor.

Due to the interest in the production of biofuels and due to the need to reduce greenhouse gas emissions, a way to integrate the above two biofuels processes would be useful. The present invention discloses processes for integrating photobioreactors with anaerobic digestion for the purpose of generating biofuels.

SUMMARY OF THE INVENTION

In the present invention, integrated processes for producing a biofuel are disclosed. Specifically, processes integrating photobioreactors with anaerobic digestion are disclosed. Anaerobic digestion can convert biomass into a biofuel. However, anaerobic digestion also produces carbon dioxide ($CO_2$). Because it is a greenhouse gas, the production of carbon dioxide is not desirable. Algae can be grown in a photobioreactor as long as light, carbon dioxide, and water are provided. In the present invention, the anaerobic digestion process is integrated with the photobioreactor process thereby providing a useful solution for the carbon dioxide that is generated and providing a source of carbon dioxide for the photobioreactor.

BRIEF DESCRIPTION OF THE FIGURE

The description is presented with reference to the accompanying figure in which:

FIG. 1 depicts a process flow diagram of one embodiment of the integrated processes of the present invention.

While the invention is susceptible to various modifications and alternative forms, specific embodiments thereof have been shown by way of example in the figure and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

In the present invention, a photobioreactor process for producing a biofuel is integrated with an anaerobic digestion process for producing a biofuel. The carbon dioxide produced from anaerobic digestion is used to grow algae in the photobioreactor. This integration both provides a source of carbon dioxide for the photobioreactor as well as finds a solution for the carbon dioxide by-product of the anaerobic digestion while producing a biofuel.

1. Definitions

Certain terms are defined throughout this description as they are first used, while certain other terms used in this description are defined below:

"Aerobic digestion," as defined herein, is a process in which microorganisms break down biological material in the presence of oxygen.

"Anaerobic digestion," as defined herein, is a process in which microorganisms break down biological material in the absence of oxygen.

"Biofuel," as defined herein, is a fuel product at least partly derived from "biomass." As used herein, biofuel encompasses hydrogen ($H_2$) and methane ($CH_4$) as well as liquid transportation fuel.

"First Generation Biofuels," as defined herein, are made from biomass feedstocks such as sugar, starch, vegetable oils, or animal fats.

"Second Generation Biofuels," as defined herein, are made from non-food crops. While terms such as "Generation N>2 Biofuels" and "Next Generation Biofuels" are increasingly used in the literature to further define non-food derived biofuels, for the purposes of this discussion, all non-food derived biofuels will be characterized "Second Generation Biofuels."

"Biomass," as defined herein, is a renewable resource of biological origin including, but not limited to, corn stover, switchgrass, agricultural wastes, municipal solid waste, and sewage. Biomass and biological residue are used interchangeably herein.

"Bioreactor," as defined herein, is a biologically active environment such as a system to grow cells.

"Photobioreactor," as defined herein, is a bioreactor with a light input. A photobioreactor typically refers to a closed system. In general, any translucent container could be a photobioreactor. For examples of photobioreactors, see Berzin, United States Published Patent Application No. 20050064577 ("Hydrogen Production with Photosynthetic Organisms and From Biodiesel Derived Therefrom"); Berzin, United States Published Patent Application No. 20050239182 ("Synthetic and Biologically-Derived Products Produced Using Biomass Produced by Photobioreactors Configured for Mitigation of Pollutants in Flue Gases"); and Berzin United States Published Patent Application No. 20050260553 ("Photobioreactor and process for Biomass Production and Mitigation of Pollutants in Flue Gases").

2. Integrated Biofuels Processes

The present invention discloses the integration of the following two biofuels processes: anaerobic digestion and photobioreactors. Anaerobic digestion can be used to produce a biofuel from biological residues. Photobioreactors can be used to produce a biofuel from algae.

Anaerobic digestion is a known process for breaking down biological material substantially in the absence of oxygen. The amount of oxygen present will be less than the amount of oxygen present in ambient air. Generally, the amount of oxygen present will be present in amounts less than 5%, and typically the amount of oxygen present will be present in amounts less than 1%. Anaerobic digestion can be used to convert biological residues from a variety of sources including, but not limited to, corn stover, municipal solid waste, and sewage. The anaerobic digestion process produces a mixture of methane and carbon dioxide. The methane is useful as a biofuel; however, the carbon dioxide is a greenhouse gas.

A photobioreactor may be used to grow cells. In one application, a photobioreactor may be used to grow algae. Inputs of light, water, and carbon dioxide are necessary for the algae to grow. Some algae are a source of triglycerides which can be extracted from the algae. The triglycerides can then be converted into a biofuel. After the extraction of the triglycerides from the algae, the remaining algae biomass residue contains sugars and proteins.

FIG. 1 depicts a process flow diagram of one embodiment of the integrated processes of the present invention. As shown in FIG. 1, biological residue 101 is converted into methane 102 and carbon dioxide 103 via anaerobic digestion in an anaerobic digester 104. The methane 102 that is produced from the anaerobic digestion is a biofuel.

Further, as shown in FIG. 1, algae 110 are grown in a photobioreactor 111. Light 112 and water 113 are supplied to the photobioreactor 111. The carbon dioxide 103 from the anaerobic digestion supplies the third required input to grow the algae 110 in the photobioreactor 111. Triglycerides 114 for biofuels production and algae biomass residue 115 are the by-products from the algae 110.

Optionally, the algae biomass residue 115 can be used as a source of biological residue 101 for the anaerobic digestion process.

Further, the water 113 in the photobioreactor 111 could act as an absorbent for the carbon dioxide 103 generated by the anaerobic digestion.

In some embodiments, under the correct conditions, the algae may produce hydrogen. In this case, the hydrogen would be considered a biofuel.

In some embodiments, the anaerobic digester may be a salt dome cavern. Salt dome caverns are substantially air-tight caverns that are known for their use as storage for both natural gas and crude oil. A salt dome cavern could also be used as an anaerobic digester. A salt dome cavern is substantially air-tight and can be large, which would accommodate significant amounts of biomass. The biomass would be able to biologically break down while in the salt dome cavern.

Illustrative embodiments of the invention are described above. In the interest of clarity, not all features of an actual embodiment are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

What is claimed is:

1. An integrated process to generate biofuels comprising:
processing a biological residue in an anaerobic digester to form a mixture of methane and carbon dioxide wherein the methane is a first biofuel, and wherein the anaerobic digester is a salt dome cavern;
supplying water, light, and the carbon dioxide formed in the salt anaerobic digester to a photobioreactor wherein the photobioreactor comprises a closed system with a light input;
growing algae in the photobioreactor wherein the algae comprises triglycerides and an algae biomass residue;
extracting the triglycerides from the algae; and
converting the triglycerides into a second biofuel.

2. The process of claim 1 wherein the biological residue processed in the anaerobic digester is agricultural wastes.

3. The process of claim 1 wherein the biological residue processed in the anaerobic digester is municipal solid waste.

4. The process of claim 1 wherein the biological residue processed in the anaerobic digester is sewage.

5. The process of claim 1 wherein the biological residue processed in the anaerobic digester is the algae biomass residue.

6. The process of claim 1 wherein the salt dome cavern operates with an amount of oxygen less than the amount of oxygen present in ambient air.

7. The process of claim 6 wherein the salt dome cavern operates with an amount of oxygen of less than 5% by volume.

8. The process of claim 6 wherein the salt dome cavern operates with an amount of oxygen of less than 1% by volume.

9. An integrated process to generate biofuels comprising:
processing a biological residue in an anaerobic digester to form a mixture of methane and carbon dioxide wherein the methane is a first biofuel, and wherein the anaerobic digester is a salt dome cavern;
supplying water, light, and the carbon dioxide formed in the salt dome cavern to a photobioreactor wherein the photobioreactor comprises a closed system with a light input;
growing algae in the photobioreactor wherein the algae produces hydrogen wherein the hydrogen is a second biofuel.

10. The process of claim 9 wherein the biological residue processed is agricultural wastes.

11. The process of claim 9 wherein the biological residue processed is municipal solid waste.

12. The process of claim 9 wherein the biological residue processed is sewage.

13. The process of claim 9 wherein the biological residue processed is the algae biomass residue.

14. The process of claim 9 wherein the salt dome cavern operates with an amount of oxygen of less than 5% by volume.

15. A system to generate biofuels comprising:
an anaerobic digester for processing a biological residue to form a mixture of methane and carbon dioxide, and wherein the anaerobic digester is a salt dome cavern; and
a photobioreactor for growing algae wherein the photobioreactor comprises a closed system with a light input;
wherein the salt dome cavern and the photobioreactor are integrated such that the carbon dioxide formed in the salt dome cavern is supplied to the photobioreactor.

16. The system of claim 15 wherein the salt dome cavern is configured to process a biological residue selected from agricultural wastes, municipal solid waste, sewage, and algae biomass residue.

* * * * *